US008007449B2

(12) United States Patent
Kotmel et al.

(10) Patent No.: US 8,007,449 B2
(45) Date of Patent: Aug. 30, 2011

(54) METHOD AND APPARATUS FOR UTERINE CAVITY LENGTH MEASUREMENT

(75) Inventors: Robert Kotmel, Burlingame, CA (US); J. Brook Burley, Sunnyvale, CA (US); Russel M. Sampson, Palo Alto, CA (US); Estela H. Hilario, Los Altos, CA (US)

(73) Assignee: Cytyc Corporation, Marlborough, MA (US)

( * ) Notice: Subject to any disclaimer, the term of this patent is extended or adjusted under 35 U.S.C. 154(b) by 1566 days.

(21) Appl. No.: 11/314,051

(22) Filed: Dec. 20, 2005

(65) Prior Publication Data
US 2007/0142750 A1  Jun. 21, 2007

(51) Int. Cl.
A61B 5/00 (2006.01)
A61B 5/103 (2006.01)
A61B 5/117 (2006.01)
A61B 17/42 (2006.01)
A61B 17/46 (2006.01)
A61D 1/10 (2006.01)
G01L 7/00 (2006.01)

(52) U.S. Cl. ........ 600/591; 600/561; 600/587; 606/119; 606/198; 73/700; 73/706

(58) Field of Classification Search .................. 600/585, 600/587, 591, 561; 606/119, 198; 73/700, 73/706
See application file for complete search history.

(56) References Cited

U.S. PATENT DOCUMENTS

| 3,312,215 A | 4/1967 | Silber |
| 3,630,190 A | 12/1971 | Baker |
| 3,706,307 A | 12/1972 | Hasson |
| 3,965,891 A | 6/1976 | Lerner |
| 4,016,867 A | 4/1977 | King et al. |
| 4,127,110 A * | 11/1978 | Bullara .................... 600/561 |
| RE30,312 E | 6/1980 | Kessel |

(Continued)

FOREIGN PATENT DOCUMENTS

CN  1060594  4/1992

OTHER PUBLICATIONS

Ole Daniel Enerson—Who Named It?, a description of *Simpson's uterine sound* (*Sir James Young Simpson*), http://www.whonamedit.com/synd.cfm/2993.html (1994-2001) (1 page).

(Continued)

*Primary Examiner* — Max Hindenburg
*Assistant Examiner* — Sean P Dougherty
(74) *Attorney, Agent, or Firm* — Robert P. Smith

(57) ABSTRACT

A uterine cavity length measuring device includes a first elongate member including a lumen and a plurality of apertures extending between the lumen and an exterior surface of the first elongate member, and a second elongate member including a lumen, and at least one aperture located at a distal end extending from the lumen of the second elongate member to an exterior surface, where the second elongate member is positioned within and is configured to move within the lumen of the first elongate member and where the first elongate member and second elongate member provide a fluid path from a proximal end of the lumen in the second elongate member, through the lumen in the second elongate member to the at least one aperture located at the distal end of the second elongate member and to at least one of the plurality of apertures in the first elongate member.

17 Claims, 9 Drawing Sheets

U.S. PATENT DOCUMENTS

| | | | | |
|---|---|---|---|---|
| 4,224,951 A * | 9/1980 | Hasson | | 600/591 |
| 4,252,131 A * | 2/1981 | Hon et al. | | 600/561 |
| 4,274,423 A * | 6/1981 | Mizuno et al. | | 600/488 |
| 4,325,387 A * | 4/1982 | Helfer | | 600/561 |
| 4,356,610 A * | 11/1982 | Hon et al. | | 29/428 |
| 4,489,732 A | 12/1984 | Hasson | | |
| 4,662,381 A | 5/1987 | Inaba | | |
| 4,712,566 A * | 12/1987 | Hok | | 600/561 |
| 4,718,423 A | 1/1988 | Willis et al. | | |
| 4,722,730 A * | 2/1988 | Levy et al. | | 604/118 |
| 4,854,330 A | 8/1989 | Evans et al. | | |
| 4,935,017 A * | 6/1990 | Sylvanowicz | | 604/532 |
| 4,944,307 A * | 7/1990 | Hon et al. | | 600/561 |
| 4,966,161 A * | 10/1990 | Wallace et al. | | 600/561 |
| 5,109,869 A | 5/1992 | Buckley | | |
| 5,113,846 A | 5/1992 | Hiltebrandt et al. | | |
| 5,184,619 A * | 2/1993 | Austin | | 600/376 |
| 5,275,610 A | 1/1994 | Eberbach | | |
| 5,279,308 A * | 1/1994 | DiSabito et al. | | 600/588 |
| 5,358,496 A | 10/1994 | Ortiz et al. | | |
| 5,415,157 A * | 5/1995 | Welcome | | 600/121 |
| 5,445,140 A | 8/1995 | Tovey | | |
| 5,566,680 A * | 10/1996 | Urion et al. | | 600/561 |
| 5,662,676 A | 9/1997 | Koninckx | | |
| 5,695,515 A | 12/1997 | Orejola | | |
| 5,984,879 A * | 11/1999 | Wallace et al. | | 600/587 |
| 6,080,118 A | 6/2000 | Blythe | | |
| 6,450,977 B1 | 9/2002 | Baxter-Jones | | |
| 7,510,533 B2 * | 3/2009 | Mauge et al. | | 600/561 |
| 2005/0101885 A1 | 5/2005 | Mulvaney | | |
| 2006/0122493 A1 * | 6/2006 | Atalar et al. | | 600/423 |

OTHER PUBLICATIONS

Pelican Healthcare Ltd., *Pelican Disposable Uterine Sound—Sterile*, Product Description, http://www.pelicanhealthcare.co.uk/sound.htm (Undated—downloaded on Mar. 31, 2005) (1 page).

Pelican Healthcare Ltd., *Pelican Disposable Sound—Technical Data Sheet*, http://www.pelicanhealthcare.co.uk/pdfs/sound.pdf (Undated—downloaded on Mar. 31, 2005) (1 page).

Westons Internet Sales, *Uterine Sound* (various products), http://westons.com/acatalog/Online_Catalogue_Uterine_sound_326.html (Last modified Feb. 23, 2005) (2 pages).

Track of Surgical, *Assorted Uterine Sounds* (various products), http://www.track.com.pk/assorted2.htm (Undated—last printed Mar. 31, 2005) (2 pages).

Life Care Supplies, *OB/GYN Instruments—Sklar Surgical Instruments—Uterine Sounds* (various products), http://lcsupplies.com/products/obgyn/sound.htm (Undated—downloaded on Mar. 31, 2005) (1 page).

Gilbert Surgical Instruments, *Sounds* (various products), http://www.gilbertsurgical.com/html/ftn/sounds.html (2000) (1 page).

International Search Report and Written Opinion of the International Searching Authority, PCT Application Serial No. PCT/US2005/043849, Apr. 20, 2006, 12 pp.

International Search Report and Written Opinion of the International Searching Authority, PCT Application Serial No. PCT/US2006/046110, Jul. 9, 2007, 11 pp.

* cited by examiner

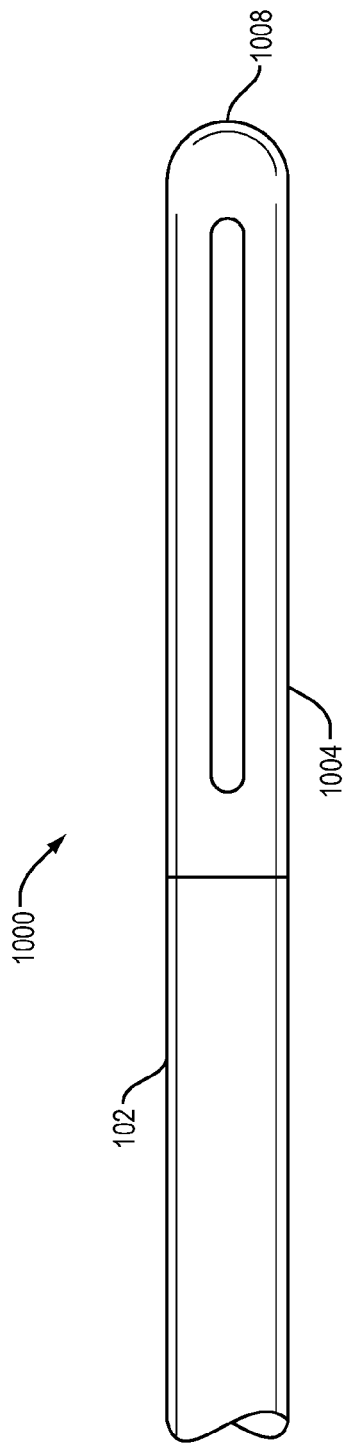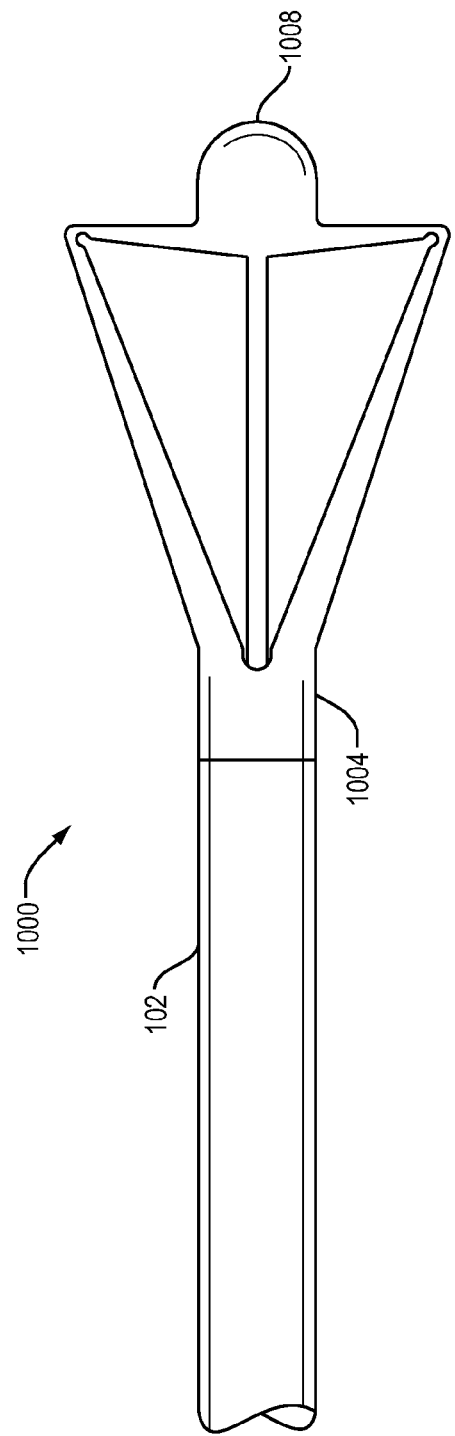

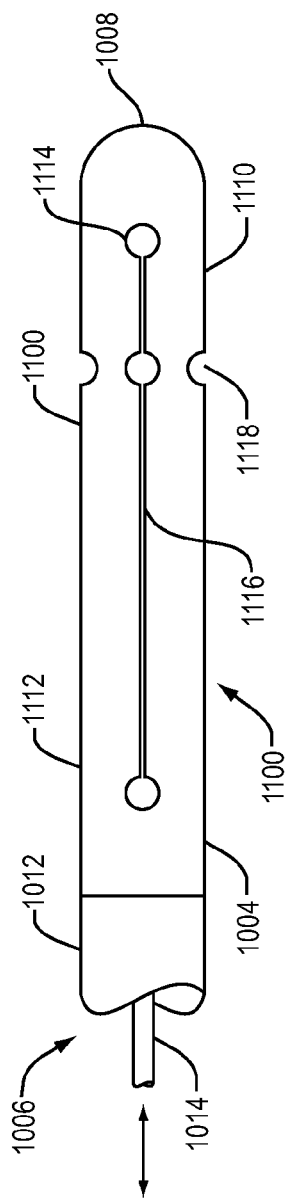
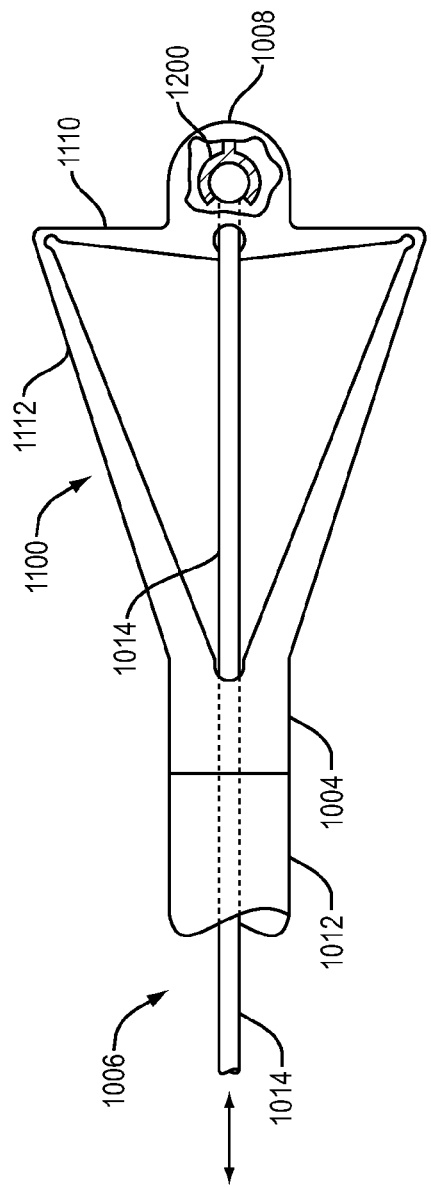
FIG. 11
FIG. 12

METHOD AND APPARATUS FOR UTERINE CAVITY LENGTH MEASUREMENT

TECHNICAL FIELD

This invention relates to medical devices and techniques.

BACKGROUND

The human uterine cavity is approximately triangular in shape and relatively flat, much like an envelope. The cavity is entered via the endocervical canal. The proximal end of the canal, the external cervical os, opens to the vagina while the distal end, the internal cervical os, opens to the uterine cavity. The tip of the triangular-shaped uterine cavity is located at the internal cervical os, while the base is defined by the openings that lead to the fallopian tubes, the tubal ostia. Sounding the uterus, i.e., determining the length from the fundus of the uterine cavity to the external cervical os, is usually a blind procedure. A physician inserts a uterine sound transcervically and advances the sound until it reaches the top, or fundus of the uterine cavity, i.e., the base of the triangle between the tubal ostia. The length from the interior fundus to the external cervical os can be measured directly using graduations stamped on the shaft of the sound. The physician relies upon tactile feedback to determine when the sound has touched the fundus.

Conventional uterine sounds are constructed from a malleable metal material, approximately 3.5 mm in diameter with a working length of roughly 25 cm, and have a flattened handle portion the physician can grasp. The uterine sound necessarily is substantially rigid in the axial direction and somewhat flexible out of plane, transverse to its axis, in order to reach the fundus and provide the physician the tactile sensation of touching the fundus.

Conventional uterine sounds provide a direct measurement of the sounding length, which includes both the uterine cavity length and the endocervical canal length. However, a physician may need to know the uterine cavity length in order to perform certain medical procedures. Conventional uterine sounds do not provide direct measurement of the uterine cavity length without additional measurements or other calculations.

SUMMARY

In general, in one aspect, a uterine cavity length measuring device is provided. The uterine cavity length measuring device includes a first elongate member including a lumen and a plurality of apertures extending between the lumen and an exterior surface of the first elongate member. The first elongate member is configured for insertion through a cervical canal with at least a portion of the first elongate member extending into a uterus. The uterine cavity length measuring device also includes a second elongate member including a lumen, a distal end, and at least one aperture located at the distal end extending from the lumen of the second elongate member to an exterior surface of the second elongate member. The second elongate member is positioned within and is configured to move within the lumen (e.g., move coaxially) of the first elongate member. The first elongate member and second elongate member provide a fluid path from a proximal end of the lumen in the second elongate member, through the lumen in the second elongate member to the at least one aperture located at the distal end of the second elongate member and to at least one of the plurality of apertures in the first elongate member. The first elongate member and second elongate member are configured such that fluid flow through the fluid path and into the uterus is permitted when the distal end of the second elongate member is positioned within a portion of the first elongate member that is positioned within the uterus. Fluid flow through the fluid path is restricted when the distal end of the second elongate member is positioned within a portion of the first elongate member that is positioned within the cervical canal.

Implementations can include one or more of the following features. The uterine cavity length measuring device can further include a fluid flow sensor configured to indicate a change in fluid flow through the fluid path. A distal end of the first elongate member includes an atraumatic tip. The distal end of the second elongate member can further include a first ring positioned distally of the at least one aperture and configured to provide a substantially airtight seal between the distal end of the second elongate member and an interior surface of the first elongate member and a second ring positioned proximally of the at least one aperture and configured to provide a substantially airtight seal between the distal end of the second elongate member and an interior surface of the first elongate member.

The first elongate member can further include one or more exhaust lumens extending from approximately a proximal end to a distal end of the first elongate member and one or more exhaust holes, each exhaust hole extending between the exterior surface of the first elongate member and at least one of the one or more exhaust lumens. The uterine cavity length measuring device can further include an air input port coupled to a proximal end of the second elongate member. A fluid flow sensor can be positioned between the proximal end of the second elongate member and the air input port. The fluid flow sensor can be a paddlewheel. The uterine cavity length measuring device can further include graduations marked on at least a portion of the length of the second elongate member configured to indicate a measurement of a length of the uterine cavity, and graduations marked on at least a portion of the length of the first elongate member configured to indicate a measurement from an external cervical os to a fundus of the uterus (i.e., the sounding length).

In general, in one aspect, a method for using a uterine cavity length measuring device is provided. The method includes inserting an outer sheath of the uterine cavity length measuring device transcervically to a fundus of a uterine cavity, the uterine cavity length measuring device including an inner member extended within the outer sheath. The method also includes initiating a fluid flow through the uterine cavity length measuring device, withdrawing the inner member relative to the outer sheath until fluid flow is reduced indicating the inner member positioned at an internal cervical os, and measuring the uterine cavity length according to the position of the inner member.

Implementations can include one or more of the following features. The method can further include withdrawing the inner member relative to the outer sheath beyond the internal cervical os, detecting a change in fluid flow indicating the inner member positioned at an external cervical os, and measuring the sounding length according to the position of the inner member.

In general in one aspect, a uterine cavity length measuring device is provided. The uterine cavity length measuring device includes a first elongate member including a lumen, the first elongate member configured for insertion through a cervical canal with at least a portion of the first elongate member extending into a uterus. The uterine measurement device also includes a second elongate member including a lumen, where the second elongate member is positioned within the lumen of the first elongate member and is configured to move within the lumen, and a fluid flow sensor configured to indicate a change in fluid flow through the lumen in the second elongate member. The fluid flow can decrease when a distal end of the second elongate member is positioned within a portion of the first elongate member that is positioned within the cervical canal as compared to the fluid flow when the distal end of the second elongate member is positioned within a portion of the first elongate member that is positioned within the uterine cavity.

Implementations of the specification can provide one or more of the following advantages. A uterine measurement device can be provided such that a user can directly measure the length of the uterine cavity. Additionally, the sounding length and/or the cervical canal length can also be directly measured.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10A shows an expandable end cap for an outer sheath of a uterine measurement device in a closed position.

FIG. 10B shows the expandable end cap for the outer sheath of FIG. 10A in an open position.

FIG. 11 shows a top view of the end cap of an outer sheath in a closed position including a control rod.

FIG. 12 shows a top view of the end cap of the outer sheath of FIG. 11 in an open position.

Like reference symbols in the various drawings indicate like elements.

DETAILED DESCRIPTION

A uterine cavity length measuring device is provided for taking a direct measurement of the length of a uterine cavity. The device includes a first elongate member including a lumen and multiple apertures extending between the lumen and an exterior surface of the first elongate member. The first elongate member is configured for insertion through a cervical canal with at least a portion of the first elongate member extending into the uterus. The device further includes a second elongate member including a lumen, a distal end, and at least one aperture located at the distal end extending from the lumen to an exterior surface of the second elongate member. The second elongate member is positioned within the lumen of the first elongate member and is configured to move within the lumen. When the distal end of the second elongate member is positioned within a portion of the first elongate member that is positioned within the uterine cavity, fluid can flow through a fluid path from a proximal end of the lumen in the second elongate member, through the lumen in the second elongate member to the at least one aperture located at the distal end of the second elongate member and to at least one of the multiple apertures in the first elongate member and into the uterine cavity. When the distal end of the second elongate member is positioned within a portion of the first elongate member that is positioned within the cervical canal, fluid flow through the fluid path is restricted.

Figure 1:
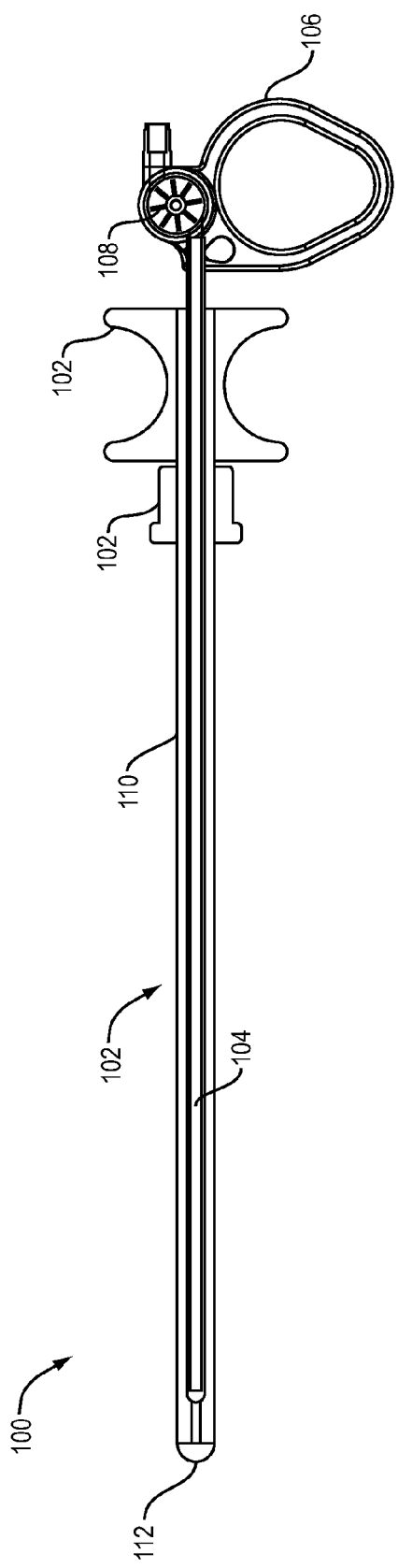
FIG. 1 illustrates a longitudinal cross section of a uterine measurement device.

One implementation of a uterine measurement device 100 is shown in FIG. 1. The uterine measurement device 100 is configured to have a first elongate member, i.e., outer sheath 102, and a second elongate member, i.e., movable inner member 104. The uterine measurement device 100 further includes a flow monitor 108 configured to detect changes in the flow of a fluid as the inner member 104 is moved within the outer sheath 102, e.g., coaxially. Under normal operating conditions, the distal end of the outer sheath 102 is initially inserted to approximately the fundus of the uterine cavity. The inner member 104 is then moved relative to the outer sheath 102 to identify the length of the uterine cavity as well as the length of the endocervical canal according to changes in fluid flow as detected by the flow monitor 108, e.g., air flow.

The outer sheath 102 includes an elongate lumen 110 having a proximal and distal end. The outer sheath 102 also includes a tip 112 that can provide an atraumatic end cap to the outer sheath 102. The atraumatic shape of the tip 112 protects against harm to the uterine wall when locating the fundus (e.g., protecting against perforation of the uterine wall).

The outer sheath 102 is configured for insertion into the uterine cavity. The outer sheath 102 is substantially rigid in a compressive direction axially with respect to the distal and proximal ends as well as non-axially. The outer sheath 102 can be rigid axially such that a user is provided a tactile sensation when the fundus is reached by the tip 112.

In one implementation, the uterine measurement device 100 can be disposable. The outer sheath 102 can be formed from injection molded thermoplastic, metal, or other material. In one implementation, the outer sheath 102 can be formed from plastics such as ABS, polystyrene, Peek, polycarbonate, or Ultem. In one implementation, the outer sheath 102 can be formed, in whole or part, by injection molding two longitudinal halves, which are then attached together, for example, through the use of an adhesive or other bonding technique. Alternatively, the outer sheath 102 can be machined from a solid rod or tube of material.

The outer sheath 102 of the uterine measurement device 100 can be molded to include a curvature suitable for easing passage of the outer sheath 102 through the uterus. The curvature of the elongate member can be configured in any number of shapes and degrees of curvature, including but not limited to for example, the average curvature of the uterus. In another embodiment, the outer sheath 102 can optionally be molded to include a desired curvature and/or be manipulated by a user to provide a desired curvature.

Figure 2:
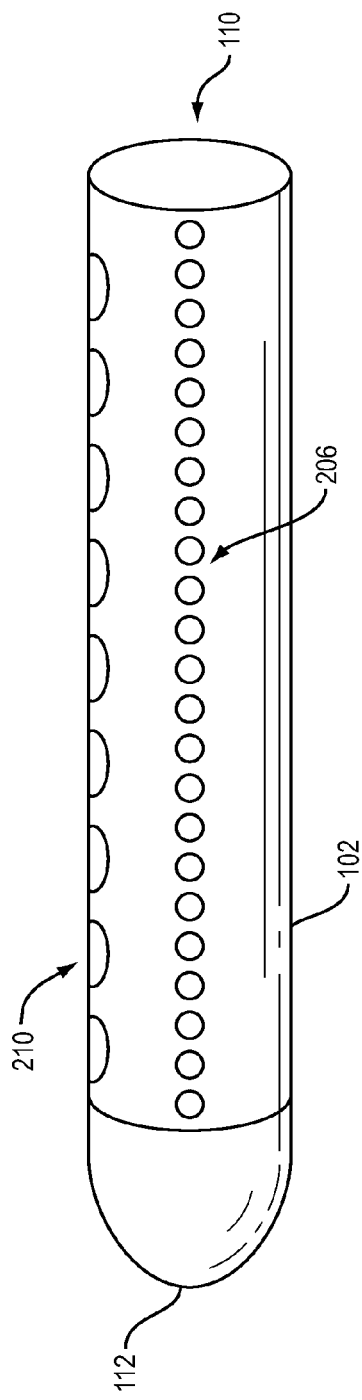
FIG. 2 illustrates a portion of an outer sheath of a uterine measurement device.

FIG. 2 shows an isometric view of a portion of the outer sheath 102. The outer sheath 102 includes a tip 112. As mentioned above, the tip 112 can provide an atraumatic surface protecting against injury from contact between the tip 112 and uterine tissue. Other tip configurations are possible including a tip configured similar to the end caps disclosed in co-pending U.S. patent application Ser. No. 11/019,500, filed on Dec. 20, 2004, which is hereby incorporated by reference in its entirety.

The outer sheath 102 includes a series of output holes 206 extending through the wall of the outer sheath 102 and into the lumen 110. In one implementation, a second series of holes can be positioned opposite the series of output holes 206, i.e., on the opposite face of the outer sheath 102. In another implementation, each hole in the series of output holes 206 is closely positioned relative to the next hole in the series. The diameter of each hole in the series of output holes 206 as well as the spacing between the output holes 206 can vary in different implementations of the outer sheath 102. The spacing and size of the holes in the series of output holes 206 can vary within the series. The spacing between the output holes 206 can be selected to provide a desired measurement accuracy. For example, in one implementation the spacing between output holes is substantially 1 mm. Additional series of output holes can also be added to the outer sheath 102. Different series of output holes can be offset from each other (e.g., by 0.5 mm) in order to increase measurement accuracy. The output holes 206, are configured to provide a path for passing a fluid (e.g., air or another gas) from the inside of the lumen 110 to outside the outer sheath 102.

In another implementation, the series of output holes 206 includes a distalmost output hole positioned substantially at the distal end of the outer sheath 102. The series of output holes 206 can extend along the outer sheath 102 toward the proximal end of the outer sheath 102. In one implementation, the series of output holes 206 extend such that the proximalmost hole is positioned substantially at the proximal end of the outer sheath 102. In another implementation, the series of output holes 206 extends along the outer sheath 102 a distance from the distal end of the outer sheath 102 that is greater than a typical uterine cavity length.

The outer sheath 102 can also include a series of exhaust holes 210. In one implementation a second series of exhaust holes can be formed on the opposite side of the outer sheath 102. The exhaust holes 210 provide a return path coupling the outside of the outer sheath 102 to an exhaust shaft (i.e., a second lumen) included within the outer sheath 102. The exhaust shaft is discussed in further detail below with respect to FIG. 3. The exhaust shaft runs longitudinally within the outer sheath 102 and is coupled to each of the exhaust holes 210. More than one exhaust shaft can be used, e.g., if more then one series of exhaust holes are included.

The exhaust holes 210 are configured to pass a fluid (e.g., air) from within the uterine cavity through the exhaust shaft and out of the uterine measurement device 100. The exhaust holes 210 can prevent the uterine cavity from becoming over inflated, while allowing incoming fluid to continue to flow into the uterine cavity from the output holes 206.

Figure 3:
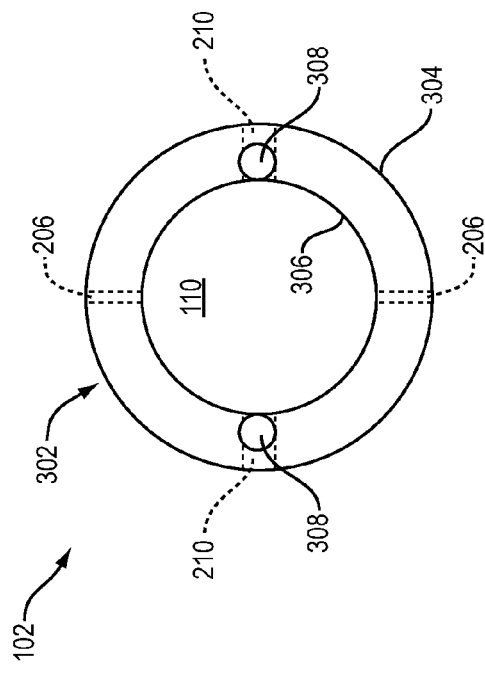
FIG. 3 illustrates a cross-sectional view of the outer sheath of a uterine measurement device.

FIG. 3 shows a cross-sectional view of one implementation of the outer sheath 102. The outer sheath includes a wall 302 having an outer surface 304 and an inner surface 306. The outer diameter of the wall 302 is configured to facilitate insertion into the uterus as well as to substantially equal the diameter of the external and internal cervical os (with or without dilation). Output holes 206 provide a path for passing a fluid between the lumen 110 and the exterior of the outer sheath 102.

The exhaust shafts 308 are positioned within the wall 302 and can run substantially the length of the outer sheath 102. In an alternative implementation, the exhaust shafts can be channels formed into the inner surface 306 of the wall 302 instead of wholly contained within the wall 302.

The exhaust holes 210 pass from the outer surface 304 of the wall 302 to the exhaust shafts 308. The exhaust holes 210 allow a fluid to pass from outside the outer sheath 102 to the exhaust shafts 308. The exhaust shafts can then pass the fluid to the proximal end of the outer sheath 102 to exit the uterine measurement device 100.

The following fluid path is thereby provided. Fluid, e.g., air, can flow from the proximal end of the outer sheath 102 up the lumen 110 and escape one or more of the output holes 206 into the uterine cavity. Fluid can then return from the uterine cavity into one or more exhaust holes 210 and pass down an exhaust shaft 308 to exit the proximal end of the outer sheath 102.

Referring back to FIG. 1, a handle 106 is coupled to the proximal end of the outer sheath 102. In one implementation, the handle 106 is an extension of the outer sheath 102. In another implementation, the handle 106 is a separate component coupled to the outer sheath 102. The handle 106 can be configured for user manipulation including finger grips or other tactile features allowing the user to hold and position the uterine measurement device 100. The handle 106 can be used to control movement of the inner member 104 relative to the outer sheath 102.

Figure 4:
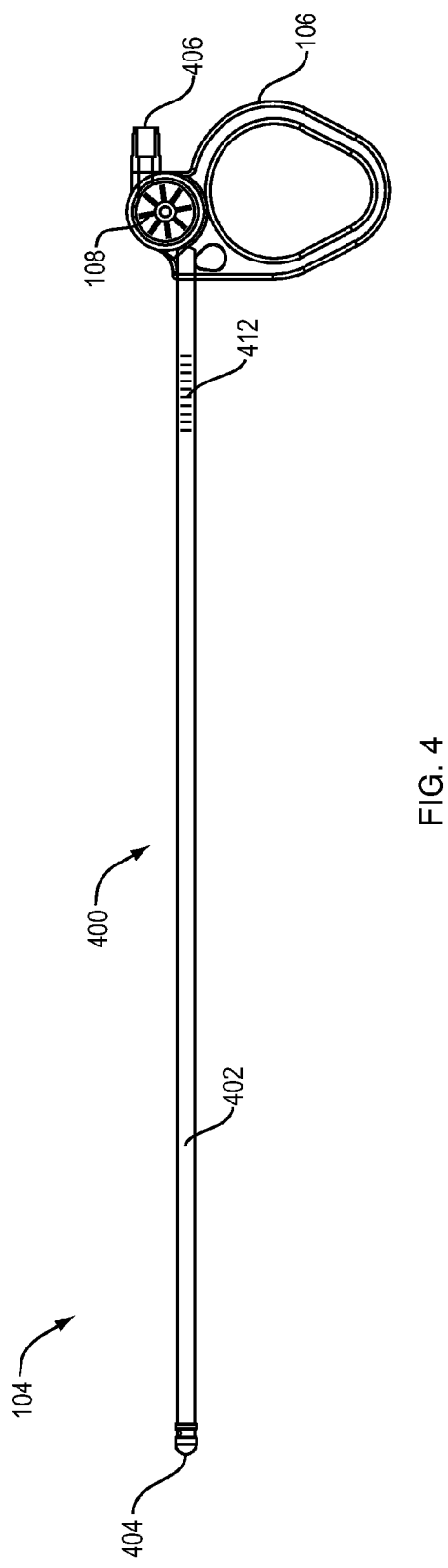
FIG. 4 illustrates a side view of a uterine measurement device with the outer sheath removed.

FIG. 4 shows a side view of the uterine measurement device 100 with the outer sheath 102 removed for illustrative purposes. FIG. 4 shows the inner member 104 that includes a shaft 400 (including a lumen 402) and a plunger tip 404. The lumen 402 includes a proximal and a distal end and is operable to pass a fluid from the proximal end to the plunger tip 404 at the distal end. The proximal end of the lumen 402 is coupled to the flow monitor 108 and the handle 106. The distal end of the lumen 402 is coupled to the plunger tip 404.

The inner member 104 can be formed from injection molded thermoplastic, metal, or other material. In one implementation, the inner member 104 can be formed from plastics such as ABS, polystyrene, Peek, polycarbonate, or Ultem. In one implementation, the inner member 104, in whole or part, can be formed by injection molding two longitudinal halves, which are then attached together, for example, through the use of an adhesive or other bonding technique. Alternatively, the inner member 104 can be machined from a solid rod or tube of material.

An input port 406 is coupled to the flow monitor 108, such that a fluid can enter the uterine measurement device 100 through the input port 406 and pass to the flow monitor 108. The lumen 402 of the inner member 104 is coupled to the flow monitor 408 such that the fluid entering the flow monitor 108 can flow through the flow monitor 108 and into the lumen 402.

The inner member 104 can include a set of graduations 412 configured to provide a direct measurement of uterine cavity length, cervical canal length or sounding length, as shall be described further below. The graduations 412 can demarcate unit measurements, for example, in centimeters, millimeters, or some other unit.

Figure 5:
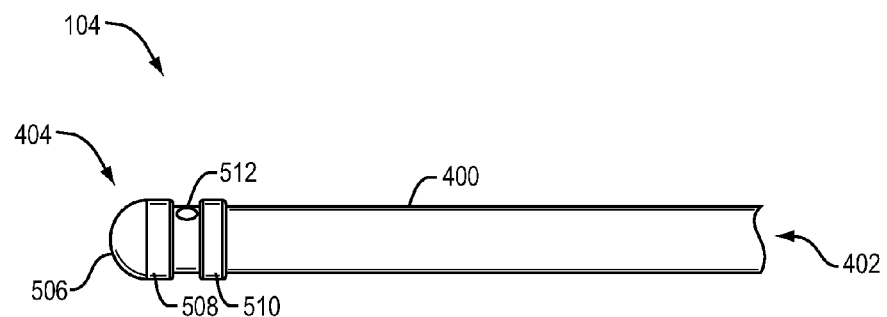
FIG. 5 illustrates a side view of a portion of an inner member of a uterine measurement device.

FIG. 5 illustrates a detailed side view of a portion of the inner member 104 including the plunger tip 404 and the shaft 400. The plunger tip 404 includes an end cap 506, a first sealing ring 508, a second sealing ring 510, and one or more exit holes 512. The end cap 506 is shown as hemispherical shaped; however, the end cap 506 can be configured in other shapes.

The first and the second sealing rings 508 and 510 are configured to provide a substantially airtight seal between the plunger tip 404 and the inner surface 306 of the outer sheath 102. In one implementation, the first and second sealing rings 508 and 510 are composed of respective o-rings positioned around the distal end of the inner member 104. In another implementation, the sealing rings 508 and 510 are each composed of a raised portion including a channel for holding an o-ring or other sealing material. The channel facilitates positioning the o-ring such that the o-ring is held in place, reducing the chance of slipping or misalignment resulting in reduced sealing ability. Additionally, the raised portion can allow the shaft 400 of the inner member 104 to have a diameter which is less than the inner diameter of the outer sheath 102, while the plunger tip 404 maintains a seal between the plunger tip 404 and the inner surface 306 of the outer sheath 102.

The exit hole 512 is positioned between the first and second sealing rings 508 and 510. The exit hole 512 is coupled to the lumen 402 such that fluid flowing through the lumen 402 can exit through the exit hole 512. In one implementation, additional exit holes can be provided. Fluid passing from the lumen 402 through the exit hole 512 can then pass through one or more output holes 206 in the outer sheath 102 and into the uterine cavity. In one implementation, the plunger tip 404 (as well as outer sheath 102) is configured such that the distance between the first and second sealing rings 508 and 510 encompasses at least two output holes 206 included in the series of output holes in the outer sheath 102, in order to provide a relatively consistent fluid flow through the uterine measurement device 100. Thus, the spacing between the first and second sealing rings 508 and 510 as well as the spacing between the output holes 206 are each configured to provide a relatively consistent flow across a limited range of the series of output holes 206 along the outer sheath 102. Consequently, changes in fluid flow due to obstruction of particular output holes 206 can be used to determine uterine cavity length.

Figure 6:
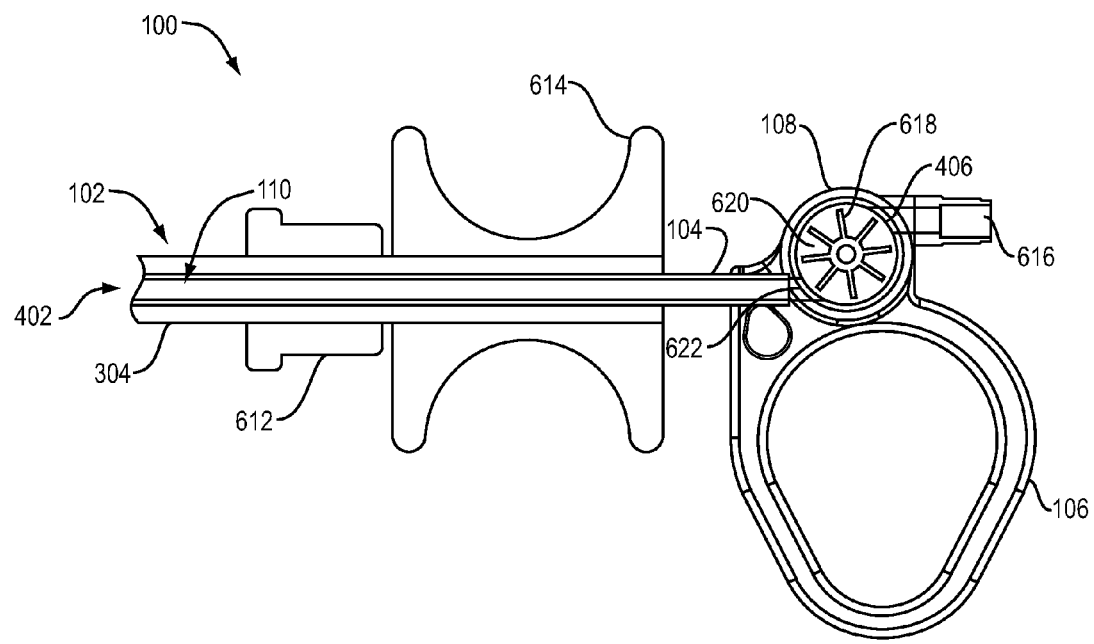
FIG. 6 illustrates a cross-sectional view of an air flow monitor and handle of a uterine measurement device.

FIG. 6 illustrates a cross-sectional view of a proximal end of the uterine measurement device 100. The outer sheath 102 includes the lumen 110, which is coupled to a movable element and a grip 614. In the implementation shown, the movable element is a movable collar 612. The collar 612 is optional and is configured to move along the outer surface 304 of the outer sheath 102 to facilitate a measurement of the sounding length, as described further below.

The grip 614 is coupled to the proximal end of the outer sheath 102. The grip 614 is configured to allow a user to hold the uterine measurement device 100 during insertion as well as to hold the outer sheath 102 of the uterine measurement device 100 in place during a measurement operation (e.g., while moving the inner member 104 relative to the outer sheath 102 using the handle 106).

The inner member 104 is coupled to an output port 622 of the flow monitor 108. The output port 622 is operable to pass a fluid from the flow monitor 108 into the lumen 402 of the inner member 104. The flow monitor 108 also includes an input port 406 coupled to an external input 616. The input port 406 is operable to pass a fluid from the external input 616 to the flow monitor 108. The external input 616 can be coupled to an external fluid source during a length measurement operation. The external fluid source can include, for example, a $CO_2$ canister, a regulated air source (e.g., a hospital wall source), an inflatable bladder system or other source.

In this implementation, the flow monitor 108 includes a cavity 620 and a paddlewheel 618. The paddlewheel 618 is configured to spin along an axis orthogonal to the fins of the paddles. The paddlewheel 618 can be mounted into the cavity 620 such that the paddles of the paddlewheel 618 align with the fluid flowing from the input port 406. The flow monitor 108 is configured such that the paddlewheel 618 rotates within the cavity 620 when the fluid flows from the input port 406 to the output port 622. Additionally, the paddlewheel 618 is configured such that changes in flow between the input port 406 and the output port 622 cause a change in rotational velocity of the paddlewheel 618. For example, in one implementation, the paddlewheel 618 can be configured such that the rotational friction requires a particular flow rate in order to cause the paddlewheel 618 to spin. The flow monitor 108 can be constructed such that a portion of the cavity is composed of a transparent or semi-transparent material allowing the user to visually observe the motion of the paddlewheel 618.

Other configurations of the flow monitor 108 can be used and the one described herein is exemplary for illustrative purposes. For example, structures other than a paddlewheel can be used to detect changes in air flow. The flow monitor 108 can also be any form of electronic, mechanical, pneumatic, or audible (e.g., whistle) sensor, which can detect or indicate changes in fluid flow (or pressure) within the flow monitor 108.

Figure 7:
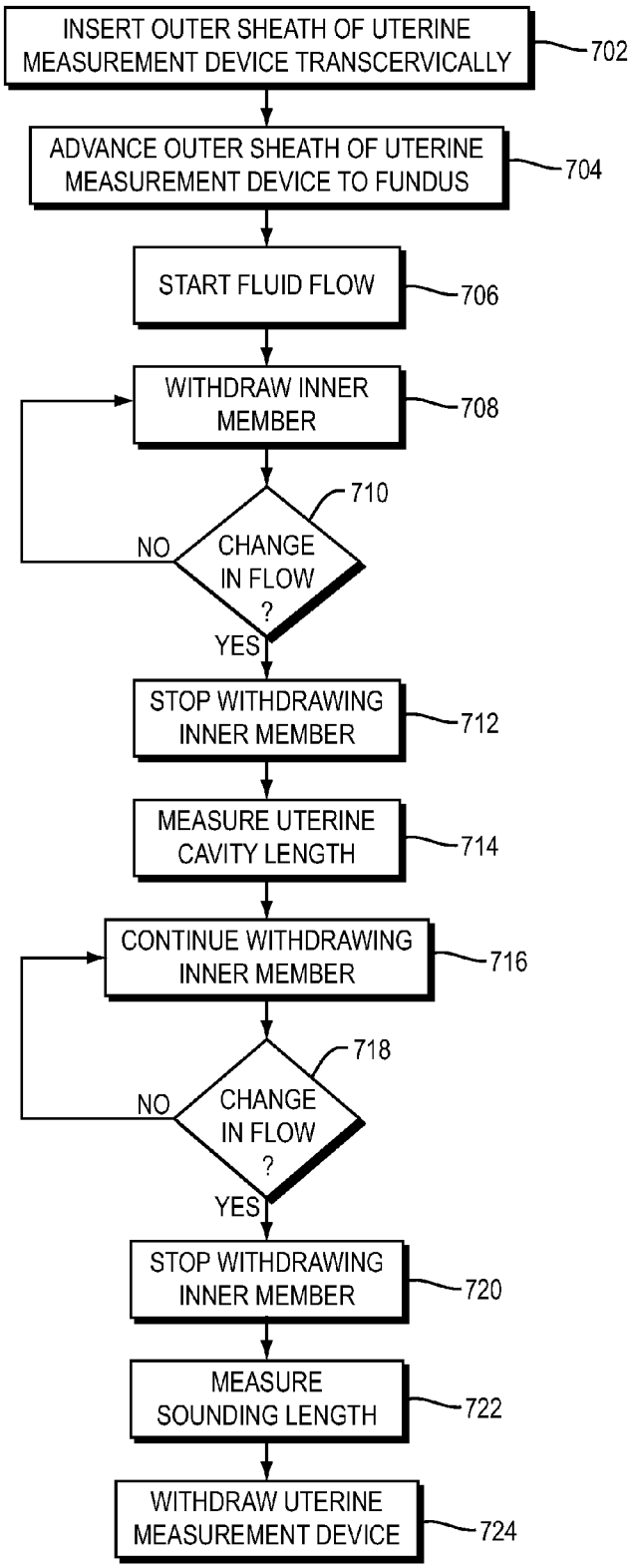
FIG. 7 is a flowchart showing a process for directly measuring a uterine cavity length.

A process 700 for using a uterine measurement device is shown in FIG. 7. For illustrative purposes, the process 700 shall be described in the context of the uterine measurement device 100 described above. However, it shall be understood that other implementations of the uterine measurement device can be used to carry out the process.

The user, for example a doctor or other medical professional, inserts the outer sheath 102 of the uterine measurement device 100 transcervically into the patient (step 702). In one implementation, the user first dilates the cervix to a diameter substantially equal to the outer diameter of the outer sheath 102.

The user advances the uterine measurement device 100 until the tip 112 of the outer sheath 102 reaches the fundus (step 704). The user can rely on tactile feedback from the uterine measurement device 100 to determine when the fundus has been reached. For example, the user can feel resistance once the tip 112 contacts the uterine wall.

Once the fundus has been reached, fluid flow into the uterine measurement device 100 is commenced (step 706). The fluid flow can be provided by coupling an external fluid source to the uterine measurement device 100. For example, the external source can be coupled to the external input 616 of the uterine measurement device 100. The fluid can be, for example, air or a gas such as nitrogen, oxygen, or carbon dioxide.

When fluid flow begins, the fluid traverses a path from the external input port 406 to the flow monitor 108. An output port 622 of the fluid monitor 108 leads into the lumen 402 of the inner member 104. The fluid travels the length of the lumen 402 to the plunger tip 404. The fluid then passes through the exit hole 512 in the plunger tip 404. Because the portion of the outer sheath 102 within which the inner member 104 is positioned within the uterine cavity, then fluid can pass through one or more output holes 206 in the outer sheath 102 and into the uterine cavity.

The uterine cavity may become partially inflated prior to the fluid re-entering the uterine measurement device 100 though the exhaust holes 210 in the outer sheath 102 and passing into the exhaust shaft 308. The fluid can then pass through the exhaust shaft 308 and exit the uterine measurement device 100 at the proximal end. In one implementation, after some initial period of time, the fluid flow equalizes such that the flow monitor 108 indicates a substantially constant fluid flow across the flow monitor 108 as fluid traverses from the external input port 406 through the uterine measurement device 100 until exiting through the exhaust shaft 308 in the outer sheath 102.

In one implementation, the user can observe the fluid flow rate by observing the speed of a paddlewheel 618 within the cavity 620 of the flow monitor 108. Alternatively, the flow monitor 108 can include a readout or display screen providing an indication of flow rate or pressure.

After the flow rate has substantially equalized, the user begins withdrawing the inner member 104 while maintaining the outer sheath 102 in the original position (i.e., with the tip 112 at the fundus) (step 708). In one implementation, the uterine measurement device 100 is inserted with the inner member 104 fully advanced within the outer sheath 102. Alternatively, the inner member 104 can be advanced fully after insertion but prior to initiating fluid flow. As the inner member 104 is withdrawn, the user can monitor the flow monitor 108 for a change in flow rate (step 710). A change in flow rate, for example, the flow rate substantially decreasing or ceasing, can indicate that the internal cervical os has been reached. Because outer sheath 102 is configured such that the outer diameter of the outer sheath 102 is substantially the same diameter as the opening provided by the internal cervical os, the tissue of the cervical canal substantially blocks the output holes 206 along the outer sheath 102 that are positioned within or at the internal cervical os.

When the plunger tip 404 is withdrawn to the internal cervical os, the fluid flow from the exit hole 512 cannot escape through the outer holes 206 in the outer sheath 102, as the outer holes 206 are blocked by the tissue of the cervix at the internal cervical os. The fluid is furthermore prevented from passing through other output holes 206 in the outer sheath 102 by the sealing rings 508 and 510 on the plunger tip 404. Consequently, when the plunger tip 404 of the inner member 104 is withdrawn to the point of reaching the internal cervical os, the fluid flow through the uterine measurement device 100 substantially ceases.

While there is no change in flow rate, the user continues to withdraw the inner member. When a flow rate change is detected, the user stops withdrawing the inner member 102 (step 712). In this implementation, the user detects a change in the fluid flow by visually observing a slowing or stopping of the paddlewheel in the flow monitor 108. However, as mentioned, different devices can be used to identify a flow reduction depending on the type of flow monitor implemented, including a gauge or digital sensor readout.

The user then directly measures the uterine cavity length (step 714). The uterine cavity length is measured according to the calibrated graduations 412 marked or imprinted along the inner member 104. The graduations indicate the distance the inner member 104 has been withdrawn relative to the tip 112 of the outer sheath 102, which has remained substantially in contact with the fundus throughout the measuring process.

The user can optionally continue withdrawing the inner member 104 to calculate the cervical canal length. To calculate the cervical canal length, the user continues withdrawing the inner member 104 (step 716) until a change in flow increase is detected by the flow monitor 108 (step 718). An increase in flow rate indicates that the plunger tip 404 has passed the external cervical os demarcating the end of the cervical canal. After passing the external cervical os, cervical tissue no longer blocks the output holes 206 in the outer sheath 102, allowing fluid flow out of the output holes 206 and into the vagina. Alternatively, a change in flow may only indicate that the plunger 404 is in the cervical canal, however the user can observe a second decrease in flow rate indicating the plunger tip at the external cervical os followed by a second, more substantial increase in flow rate.

The user stops withdrawing the inner member when the increase in flow rate is detected (step 720). The user then calculates the cervical canal length (step 722), which is the distance between where the fluid flow initially decreased (i.e., the internal cervical os) and the point where the fluid flow substantially increased (i.e., the external cervical os). The user can record the position of the plunger tip 404 according to the graduations 412 marked or imprinted along the inner member 104. This value is the sounding length, i.e., the value from the external cervical os to the fundus. Alternatively, the cervical canal length can be calculated by subtracting the uterine cavity length from the sounding length.

After completing the desired measurements, the user can withdraw the uterine measurement device 100 (step 724). In one implementation, the user first halts the fluid flow into the uterine measurement device prior to removal of the uterine measurement device 100. The user can also return the inner member 104 to the starting position (e.g., fully advanced into the outer sheath 102) in order to facilitate the withdrawal of the uterine measurement device 100.

In an alternative implementation, the measurements can be performed in a reverse order. For example, the uterine measurement device 100 can be inserted and the inner member 104 withdrawn prior to beginning fluid flow. The user can then move the plunger tip 404 of the inner member 104 toward the tip 112 of the outer sheath 102, which is positioned at approximately the fundus. Again, by detecting changes in fluid flow rate, the user has an indication of when the plunger tip has passed the internal cervical os and entered the uterine cavity.

In one implementation, the user can measure only the uterine cavity length or both the uterine cavity length and the cervical canal length or the sounding length. If the user is measuring the sounding length or cervical canal length in addition to the uterine cavity length, the user advances the inner member until the flow decreases indicating the plunger tip has reached the external cervical os (and therefore the beginning of the cervical canal). The user can then record the position according to the graduations on the inner member.

The user then continues to advance the inner member until the flow increases; indicating the plunger tip 404 has reached the internal cervical os. The position of the plunger tip 404 according to the graduations 412 allows the user to calculate the cervical canal length (e.g., the difference between the graduation readings indicates the cervical canal length). Additionally, the position of the plunger tip 404 provides the uterine cavity length since the graduations 412 are calibrated relative to the tip 112 of the outer sheath 102, which is in contact with the fundus.

In another implementation, the uterine measurement device 100 can directly measure the sounding length using the movable collar 612 (FIG. 6). For example, the uterine measurement device 100 can be inserted transcervically such that the tip 112 of the outer sheath 102 is positioned at approximately the fundus. The user can then adjust the position of the movable collar 612 along the outer sheath 102 (e.g., by sliding the collar towards the distal end) until the movable collar 612 is positioned at the external cervical os. A set of graduation along distal portion of the outer sheath 102 can then be used to directly measure the sounding length based on the position of the movable collar 612.

Figure 8A:
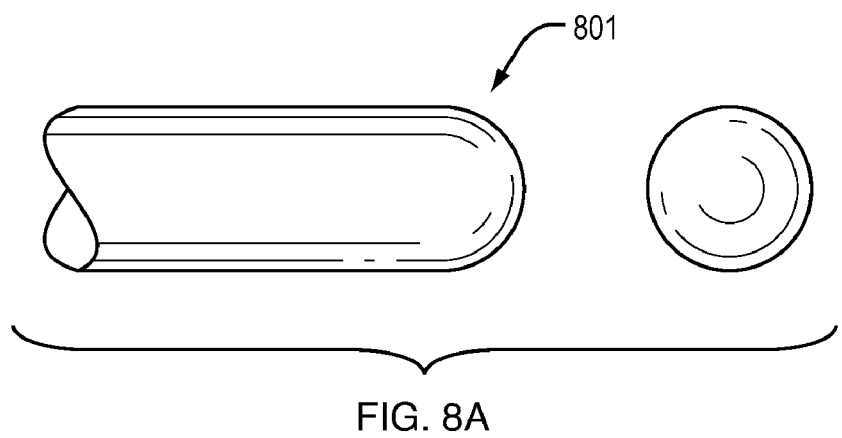
FIG. 8A shows side and end views of a full radius tip of a uterine measurement device.
Figure 8B:
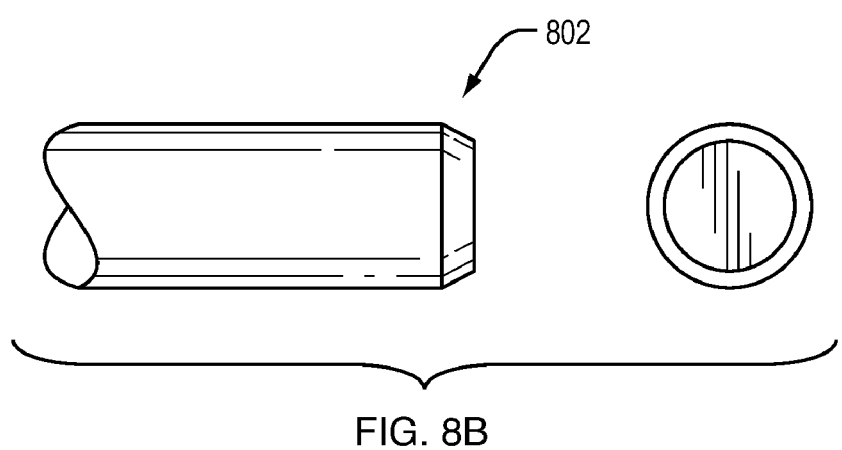
FIG. 8B shows side and end views of a chamfered tip of a uterine measurement device.
Figure 8C:
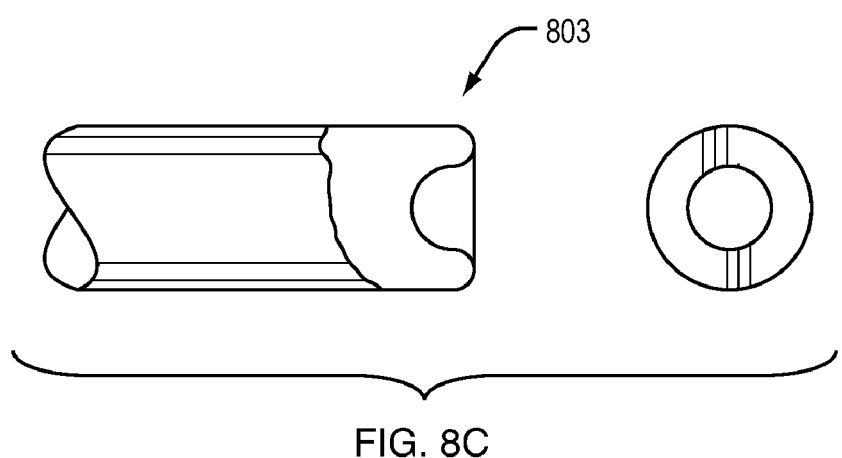
FIG. 8C shows side and end views of a concave tip of a uterine measurement device.

As mentioned above, the uterine measurement device can be configured with differently shaped tips 112. Referring to FIGS. 8A-C and 9A-C, three implementations of a tip 801, 802 and 803 are shown. The distal tips 801-803 include atraumatic geometry configured to resist perforation of the uterine wall 900 by reducing stress on the uterine wall 900. The examples of atraumatic geometry that are shown in FIGS. 8A-C, include a full radius tip 801, a chamfered tip 802 and a concave tip 803 respectively.

Figure 9A:
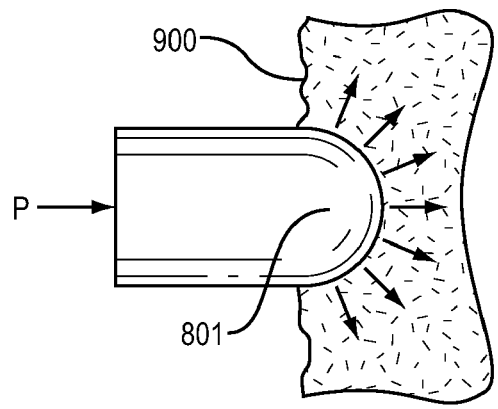
FIG. 9A shows a full radius tip of a uterine measurement device producing an axial load on a uterine wall.
Figure 9B:
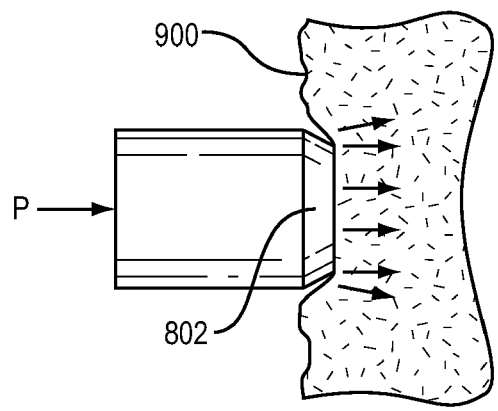
FIG. 9B shows a chamfered tip of a uterine measurement device producing an axial load on a uterine wall.
Figure 9C:
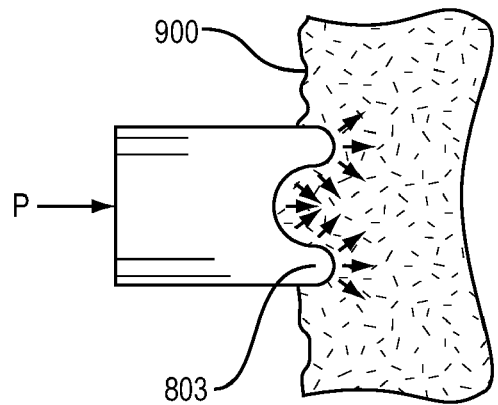
FIG. 9C shows a concave tip of a uterine measurement device producing an axial load on a uterine wall.

As shown in FIGS. 9A-C, different atraumatic distal tip geometries produce different axial loads P on the uterine wall 900. FIG. 9A illustrates the forces on the uterine wall 900 (shown as arrows) by a distal tip 801 configured as a full radius tip. FIGS. 9B and 9C similarly illustrate the forces on the uterine wall 900 by distal tips configured as a chamfered tip 802 and a concave tip 803 respectively. A full radius tip 801 as shown in FIG. 9A, resists scraping the uterine wall 900 during insertion into the uterus, but can tend to divide tissue when an axial load is applied. A chamfered tip 802, as shown in FIG. 9B, resists scraping the uterine wall 900 moderately well and better resists puncturing the wall 900 relative to a full radius tip 801. A chamfered tip 802 tends to create less radial force (indicated by arrows) in tissue, in comparison to a full radius tip 801 as shown in FIGS. 9A and 9B. A concave tip 803 can significantly protect against scraping and puncturing the uterine wall 900 and tends not to divide tissue. As shown in FIG. 9C, although the concave tip 803 does generate some radial forces (indicated by arrows) that develop tensile hoop stress on the outer perimeter, the hoop stress produced in the central region is compressive (indicated by arrows).

In an alternative implementation, a uterine measurement device can be provided that includes an outer sheath having an end cap at the distal end that can have an open position and a closed position. The end cap can be in the closed position during insertion into the uterus. Under conditions where there is a risk of the uterine measurement device perforating the uterine wall, the end cap automatically switches to the open position. The open position provides an enlarged surface area of the distal end of the inner member of the uterine measurement device that is in contact with the uterine wall and resists perforation of the uterine tissue.

Referring to FIGS. 10A and 10B, one embodiment a distal portion of a uterine measurement device 1000 is shown. The distal portion includes an outer sheath 102 and an end cap 1004. The end cap 1004 has an open and a closed position. In FIG. 10A the end cap 1004 is in a closed position, and is configured to facilitate insertion into a uterus. In FIG. 10B the end cap 1004 is in an open position; the end cap 1004 has changed geometry from having a relatively small distal tip to having an enlarged surface area.

Figure 13:
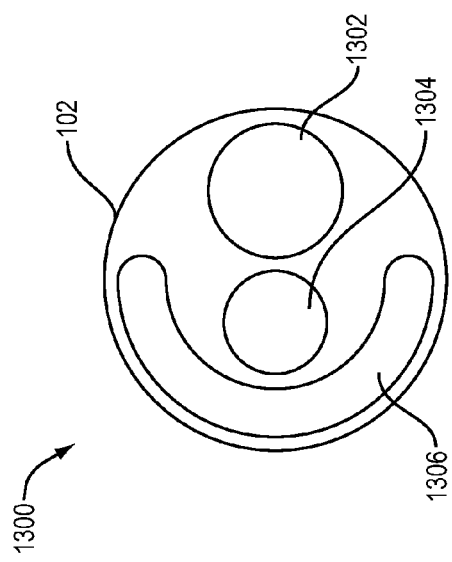
FIG. 13 shows one implementation of a cross-section for an outer sheath including an expandable end cap.
Figure 14:
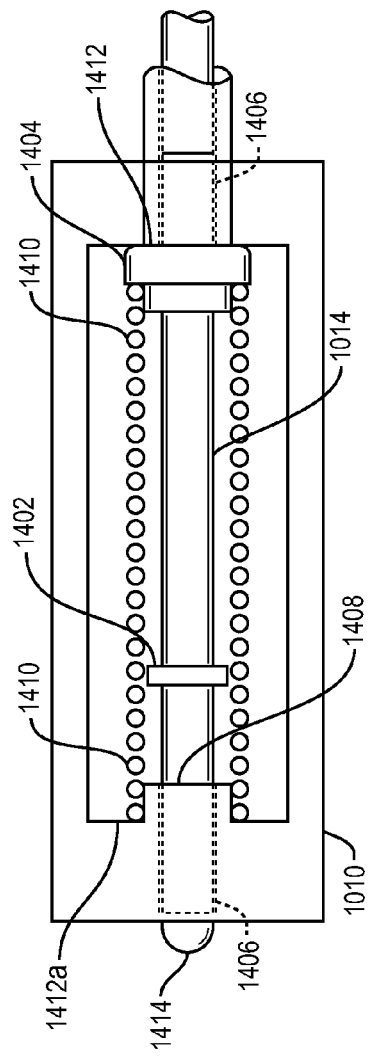
FIG. 14 is a cutaway view of a handle of a uterine cavity length measurement device including the expandable end cap shown in FIGS. 10A and 10B.

As shown in FIGS. 10A and 10B, the end cap 1004 is connected to the distal end of the outer sheath 102. The end cap 1004 can be configured in a closed position for when the outer sheath 102 is inserted into the uterus and when sounding the uterus under normal conditions (see FIG. 10A). The end cap 1004 can further be configured to automatically switch into an open position of enlarged surface area when a force is applied to a distal tip 1008 of the end cap 1004 by the uterine tissue in excess of a threshold force (see FIG. 10B). That is, the surface area of the end cap 1004 projected onto a plane substantially perpendicular to a longitudinal axis of the outer sheath 102 is enlarged in the open position. In the open position the enlarged geometry of the end cap 1004 resists penetration of the uterus by the outer sheath 102. Additionally, the end cap 1004 can be configured to automatically switch back to the closed positioned when the force is relieved from the distal tip 1008. For example, the end cap 1004 can include a degree of elasticity causing the end cap 1004 to return to the closed position when the distal tip 1008 is not acted upon by a threshold force. In an alternative implementation, the end cap 1004 can be closed manually through operation of a control rod, as discussed below. Referring also to FIG. 11, in the embodiment depicted, the outer sheath 102 includes a rod 1014 disposed within a lumen of the outer sheath 102. The rod 1014 spans the length of the outer sheath 102 and is attached to the distal end of the end cap 1004. Referring to FIG. 12, in one embodiment the rod 1014 is attached to the distal tip 1008 of the end cap 1004 by a snap fit 1200 connection. The snap fit 1200 can be in the form of a clevis-type coupling (see FIG. 12) a threaded feature, a pin, a bonding agent or any other suitable means. Where the snap fit 1200 is a clevis snap fit, a rotational degree of freedom can be provided between the rod 1014 and the distal tip 1008 of the end cap 1004. The rod 1014 can be positioned within a lumen of the outer sheath 102, non-centrally, such that the rod 1014 does not interfere with the inner member 104 of a uterine measurement device 100 such as shown in FIG. 1. FIG. 13 shows a cross-section 1300 of an outer sheath 102 including shafts for both the rod 1014 and the inner member 104. FIG. 13 includes exhaust shaft 1306 similar to the exhaust shaft discussed above, a control rod shaft 1302, and an inner member shaft 1304. The shafts are positioned to allow independent operation of the inner member 104 and the rod 1014 during a uterine measurement operation. The exhaust shaft 1306 and inner member shaft 1304 can both terminate at substantially the proximal end of the end cap 1004. The rod 1014 can be coupled to handle 1010 shown in FIG. 14. The handle 1010 can be coupled the flow monitor (e.g., flow monitor 108 of the uterine measurement device). Referring to FIG. 14, a cross-sectional view of the handle 1010 is shown. The rod 1014 can include a hardstop 1402 attached to the rod 1014 for limiting translational movement of the rod within the handle 1010. Also shown in FIG. 14, a retainer 1404 can be attached to the rod 1014 within the handle 1010, which is described further below. Referring to FIGS. 11 and 12, the end cap 1004 can include one or more deployable fins 1100 that provide a convertible arrangement for the end cap 1004 between a closed position (see FIG. 11) and an open position (see FIG. 12). The open position provides an enlarged surface area at the distal end of the inner member 1002. Deployment of the end cap 1004 to the open position is triggered when a force exceeding a threshold force is exerted on the distal tip 1008 of the end cap 1004 and transmitted down the shaft 1012. That is, when the outer sheath 102 reaches the end of the uterus, or another portion of uterine wall, and a user continues pushing on the proximal end of the outer shaft 102, if the resisting force exerted by the uterine wall on the end cap 1004 exceeds the threshold force, then the open position is triggered. As shown in FIG. 12, in one embodiment, when the open position is triggered, two fins 1100 deploy radially outwardly to provide an enlarged surface area. The fins 1100 can be formed from shorter links 1110 and longer links 1112. The length of the shorter links 1110 relative to the longer links 1112 can follow an approximate 1:3 ratio. Additionally, where the deployed shorter links 1110 are substantially perpendicular to the long axis of the outer sheath 102, the longer links 1112 are disposed at an angle including but not limited to, for example 25-30 degrees. In one embodiment, the shorter links 1110 are approximately 0.25 to 1 centimeter in length, while the longer links 1112 are approximately 0.75 to 3 centimeters in length. In another embodiment, the shorter links 1110 are approximately 0.7 centimeters in length and the longer links 1112 are approximately 2.1 centimeters in length. The outward deployment of the shorter links 1110 can include rotation of the shorter links 1110 through a larger angle than that rotated through by the connected longer links 1112. Particularly, the shorter links 1110 can be configured to deploy substantially 90 degrees to the long axis of the elongate member 1006, while the longer links 1112 deploy substantially 30 degrees to the long axis of the elongate member 1006 (see FIG. 12). The deployed shorter links 1110 and longer links 1112 create a substantially rigid, stable triangular configuration capable of withstanding substantial loads without buckling.

The shorter links 1110 and longer links 1112 of the fins 1100 can be injection molded links, pinned rigid links, resilient wire or other suitable formed links. When the end cap fins 1100 are injection molded, the end cap 1004 can have one or more slots 1116 defining fin 1100 width and one or more holes 1114 in the slot 1116. The holes 1114 are configured to define shorter link 1110 and longer link 1112 length, and provide an area of increased bending stress, thereby providing a "living hinge" at the ends of the fins 1100. A living hinge can be, for example, a molded thin flexible bridge of material (e.g., polypropylene or polyethylene) that joins two substantially rigid bodies together. Additional one or more holes 1118 in the end cap 1004 located adjacent to the one or more slots 1116, can be configured to enhance the living hinge separating the shorter links 1110 and longer links 1112.

The uterine measurement device 1000 can include a feature to sense when to switch from a closed to an open position, and a feature to deploy into the open position. In the embodiment shown, a mechanical deployment mechanism both senses when a threshold force is exceeded and automatically deploys the fins 1100 into the open position. Referring again to FIGS. 10 and 14, the deployment mechanism can be a mechanical assembly, housed within the handle 1010. The handle 1010 is attached to the outer sheath 102 at or substantially near to the proximal end. Other deployment mechanisms for converting from the closed position to the open position can be used, including electrical means by incorporating a force sensitive resistor (FSR) at the distal tip 1008. When the force exerted against the FSR exceeds a threshold value, the resistance of the FSR changes from one state to a different state. A detector located, for instance, in the handle 1010 can detect the change and trigger the release of a braking means holding the rod 1014 in place, allowing the end cap 1004 to deploy. Still another embodiment can employ a pneumatic means, whereby the force applied at the distal tip translates through the rod 1014, which could in turn bear on a plunger in a reservoir inside handle 1010. When the pressure inside the reservoir reaches the threshold value, a pressure releasing means could trigger the end cap 1004 to change to its deployed condition.

An orientation indicator can be provided to indicate to a user the proper orientation of the outer sheath 102 relative to the uterus. For example, where the fins 1100 of the inner member 1002 deploy in a plane, the proper orientation substantially aligns the plane with the plane of the substantially flat uterus to ensure safe deployment of the fins 1100. The orientation indicator can be positioned substantially near the proximal end of the outer sheath 102. The orientation indicator can be a marking on the surface, or a tactile indicator at the proximal end of the outer sheath 102. In one embodiment, the proximal end of the handle 1010 can include an orientation indicator in the form of a flattened planar side that coincides with the plane of deployment of the fins 1100. In one embodiment, the plane of handle 1010 itself can indicate the plane of deployment of the fins 1100.

In the embodiment shown in FIG. 14, the mechanical assembly included within the handle 1010 includes journals 1406 for providing a single translational degree of freedom to the rod 1014, and a boss 1408 for contacting the hardstop 1402 of the rod 1014, thereby limiting the translational movement of the rod 1014. The mechanical assembly further includes a means to govern the threshold force required to trigger conversion to the open position, e.g., to deploy the fins 1100. In the embodiment depicted, the means for governing the threshold force include a spring 1410, e.g., a compression spring. The spring 1410 can be preloaded between the handle wall 1412*a* at the handle's proximal end and the retainer 1404 connected to the rod 1014 near the handle wall 1412*b* at the handle's distal end. The retainer 1404 is constrained by the adjacent handle wall 1412*b* to maintain the spring 1410 preload. Alternatively, the governing means can include a pressurized gas in a cylinder formed within handle 1010, wherein retainer 1404 can be configured as a piston capable of translating through the cylinder.

When a uterine measurement device incorporating an end cap 1004 as shown in FIGS. 10A-B is inserted into a uterus, and the distal tip 1008 of the end cap 1004 presses against a uterine wall, a resistance force exerted by the uterine wall 600 (see FIG. 8A-C) on the distal tip 1008 is transmitted along the rod 1014 to the retainer 1404. Typically, measurement of the uterus length presents little risk of perforation using the uterine measurement device, since the end of the uterus can be identified by tactile sensation without exceeding the threshold force.

Under certain circumstances, e.g., through inadvertence, accident, anatomical divergence or stenosis of the uterus, the measuring process can result in forces on the uterine wall 600 that could perforate the uterus with the uterine measurement device. Once a force approaching, but substantially lower than a force capable of perforating the uterine wall 600, i.e., the threshold force, is transmitted to the retainer 1404, the force preloaded in the spring 1410, i.e., the threshold force, begins to compress the spring 1410. As the spring 1310 compresses, the retainer 1404 moves away from the adjacent handle wall 1412*b* and translates the rod 1014 through the journals 1406. The rod's translation is limited by the hardstop 1402 contacting the boss 1408. The translation of the rod 1014 relative to the shaft 1012 draws the distal tip 1008 of the end cap 1004 toward the handle 1010, thereby deploying the fins 1100 (see FIG. 12) and creating the desired enlarged surface area for resisting penetration of the end cap 1004 into the uterine wall 600. The inner member 104 can be calibrated according to the length of the end cap 1004 in the open position for measuring the uterine cavity length. Thus, when the inner member 104 is fully extended and the end cap 1004 is in the open position against the uterine wall, 600, the uterine measurement device reads a zero length.

After deployment, the fins 1100 of the end cap 1004 can be returned to the undeployed state by e.g., physically pushing the proximal end of the rod 1014 to the undeployed position, thereby returning the distal tip 1008 of the end cap 1004 and accordingly the fins 1100 to their undeployed positions. Alternatively, in the embodiment depicted, once the force on the distal tip 1008 of the end cap 1004 is released, i.e., is less than the threshold force, the spring 1410 expands and automatically contracts the fins 1100. Once returned to the undeployed position, the uterine measurement device 1000 can safely be removed. Alternatively, the end cap 1004 can automatically return to the undeployed position when the force of the uterine wall 600 is removed.

Referring again to FIGS. 10 and 14, the outer sheath 102 can optionally include an indicator to indicate to a user of the uterine measurement device that the threshold force was exceeded and that the end cap 1004 has converted to the open position. In the embodiment depicted, the indicator is a protrusion 1414 from the handle 1010 that is continuously connected to the rod 1014. When the threshold force of the end cap 1004 is exceeded, translation of the rod 1014 causes the protrusion 1414 to further protrude from the handle 1010, thereby providing a signal or alert to the user. In other embodiments, the indicator can be both visual and audible and can be a mechanical or an electric device or a combination of the two. For example, where the indicator is the protrusion 1414, a colored section (e.g., yellow or red) can be revealed upon exceeding the threshold force when the indicator is caused to protrude further from the handle 1010 (not shown).

Alternative techniques can also be used to provide the measurement of the uterine cavity length. For example, electronic circuitry can be used. In one implementation, electrical contacts can be positioned at a predefined spacing along the exterior surface of the inner member. The spacing interval can correspond to a desired measurement interval. Additionally, the interval can decrease as the distance from the proximal end of the inner member increases in order to provide increased measurement accuracy within a typical uterine cavity length range. Corresponding electrical contacts can be positioned on an interior surface of the outer sheath (e.g., positioned on the surface of the inner circumference of the outer sheath). The electrical contacts can be positioned at substantially the proximal end of the outer sheath (i.e., where a uterine cavity length measurement is most likely to occur). As the inner member moves relative to the outer sheath, the electrical contacts of the inner member mate with corresponding electrical contacts of the outer sheath in order to complete an electrical circuit. Logic associated with the various circuit pathways can determine the distance traversed by the inner member according to the electrical contacts on the inner member that are activated. In one implementation, a display, e.g., an LCD screen, can be used to provide a digital display to a user of the distance traversed. Thus, when the user notes that the fluid flow rate has changed, e.g., decreased at the internal cervical os, the user can read the distance measurement from the display, which measurement corresponds to the uterine cavity length. The above described example of using an electronic distance detector is merely exemplary, and other configurations of electronic detectors an be used.

In another implementation, the electronic circuitry described above can be used in conjunction with an electronic fluid flow rate detector. When there is a significant change in the fluid flow rate, i.e., an increase or decrease, the distance traversed by the inner member can be automatically displayed to a user, thereby displaying the uterine cavity length and/or the sounding length. The cervical canal length can be automatically calculated by logic associated with the circuitry, and also displayed to the user.

A number of embodiments of the invention have been described. Nevertheless, it will be understood that various modifications may be made without departing from the spirit and scope of the invention. For example, the steps shown in the flowchart of FIG. 7 can be performed in a different order and still achieve desirous results. Accordingly, other embodiments are within the scope of the following claims.

What is claimed is:

1. A uterine cavity length measuring device, comprising:
    a first elongate member including a lumen and a plurality of apertures extending between the lumen and an exterior surface of the first elongate member, the first elongate member configured for insertion through a cervical canal with at least a portion of the first elongate member extending into a uterine cavity; and
    a second elongate member including a lumen, a distal end, and at least one aperture located at the distal end extending from the lumen of the second elongate member to an exterior surface of the second elongate member, where the second elongate member is positioned within and is configured to move within the lumen of the first elongate member;
    wherein the first elongate member and second elongate member provide a fluid path from a proximal end of the lumen in the second elongate member, through the lumen in the second elongate member to the at least one aperture located at the distal end of the second elongate member and to at least one of the plurality of apertures in the first elongate member, the first elongate member and second elongate member being configured such that fluid flow through the fluid path and into the uterine cavity is permitted when the distal end of the second elongate member is positioned within a portion of the first elongate member that is positioned within the uterine cavity and such that fluid flow through the fluid path is restricted when the distal end of the second elongate member is positioned within a portion of the first elongate member that is positioned within the cervical canal.

2. The uterine cavity length measuring device of claim 1, further comprising:
    a fluid flow sensor configured to indicate a change in fluid flow through the fluid path.

3. The uterine cavity length measuring device of claim 1, where a distal end of the first elongate member includes an atraumatic tip.

4. The uterine cavity length measuring device of claim 1, where the distal end of the second elongate member further comprises:
    a first ring positioned distally of the at least one aperture and configured to provide a substantially airtight seal between the distal end of the second elongate member and an interior surface of the first elongate member; and
    a second ring positioned proximally of the at least one aperture and configured to provide a substantially airtight seal between the distal end of the second elongate member and an interior surface of the first elongate member.

5. The uterine cavity length measuring device of claim 1, where the first elongate member further comprises:
    one or more exhaust lumens extending from approximately a proximal end to a distal end of the first elongate member; and
    one or more exhaust holes, each exhaust hole extending between the exterior surface of the first elongate member and at least one of the one or more exhaust lumens.

6. The uterine cavity length measuring device of claim 1, further comprising:
    an air input port coupled to a proximal end of the second elongate member.

7. The uterine cavity length measuring device of claim 6, further comprising:
    a fluid flow sensor positioned at the proximal end of the second elongate member and fluidly coupled to the air input port.

8. The uterine cavity length measuring device of claim 7, where the fluid flow sensor comprises a paddlewheel.

9. The uterine cavity length measuring device of claim 1, further comprising:
    graduations marked on at least a portion of the length of the second elongate member configured to indicate a measurement of a length of the uterine cavity.

10. The uterine cavity length measuring device of claim 1, further comprising:

graduations marked on at least a portion of the length of the first elongate member configured to indicate a measurement of from an external cervical os to a fundus of the uterus.

11. The uterine cavity length measuring device of claim 1, where the fluid is air.

12. A uterine cavity length measuring device comprising:
   a first elongate member including a lumen, the first elongate member configured for insertion through a cervical canal with at least a portion of the first elongate member extending into a uterine cavity;
   a second elongate member including a lumen, where the second elongate member is positioned within the lumen of the first elongate member and is configured to move within the lumen of the first elongate member; and
   a fluid flow sensor configured to indicate a change in fluid flow through the lumen in the second elongate member, where the fluid flow decreases when a distal end of the second elongate member is positioned within a portion of the first elongate member that is positioned within the cervical canal as compared to the fluid flow when a distal end of the second elongate member is positioned within a portion of the first elongate member that is positioned within the uterine cavity.

13. A uterine cavity length measuring device, comprising:
   a first elongate member including a lumen, the first elongate member configured for insertion through a cervical canal with at least a portion of the first elongate member extending into a uterine cavity;
   a second elongate member including a lumen, where the second elongate member is positioned within the lumen of the first elongate member and is configured to move within the lumen of the first elongate member;
   an end cap connected to the distal end of the first elongate member, the end cap being in a closed position when the first elongate member is inserted into the uterine cavity and switching into an open position when a force applied to a distal tip of the end cap by uterine tissue exceeds a threshold force, where a surface area of the end cap projected onto a plane substantially perpendicular to the longitudinal axis of the first elongate member is enlarged in the open position as compared to in the closed position, and where the open position resists penetration of the end cap into uterine tissue; and
   a fluid flow sensor configured to indicate a change in fluid flow through the lumen in the second elongate member.

14. The uterine cavity length measurement device of claim 13, wherein the end cap includes one or more fin members, where the fin members are positioned along a longitudinal axis of the first elongate member when the end cap is in the closed position and deploy laterally from the longitudinal axis when switching into the open position.

15. The uterine cavity length measurement device of claim 13, further comprising:
   a deployment mechanism, configured to switch the end cap from the closed position to the open position upon a force on the distal tip of the end cap exceeding the threshold force.

16. The uterine cavity length measurement device of claim 15, wherein:
   the end cap includes one or more fin members, where the fin members are positioned along a longitudinal axis of the first elongate member when the end cap is in a closed position and deploy laterally from the longitudinal axis when switching into the open position;
   the first elongate member includes a rod connected to the distal tip of the end cap; and
   the deployment mechanism includes a spring positioned about the first elongate member, the spring preloaded to exert the threshold force on a first face of a retainer connected to the rod, where the threshold force exerted by the spring prevents the rod from translating in a direction away from the end cap and where the retainer includes a second face abutting a housing preventing translation of the rod in a direction toward the end cap,
   wherein when a force on the distal end of the end cap by uterine tissue exceeds the threshold force, the rod translates axially compressing the spring and thereby translating the distal end of the end cap causing the one or more fin members to deploy laterally switching the end cap into the open position.

17. The uterine cavity length measuring device of claim 13, further comprising;
   an indicator configured to provide an indication to a user when the end cap has switched from the closed to the open position.

* * * * *